United States Patent [19]

Grove

[11] 4,311,515

[45] Jan. 19, 1982

[54] SUBSTITUTED DIPHENYL ETHERS HAVING HERBICIDAL ACTIVITY

[75] Inventor: William S. Grove, Doylestown, Ohio

[73] Assignee: PPG Industries, Inc., Pittsburgh, Pa.

[21] Appl. No.: 172,319

[22] Filed: Jul. 25, 1980

[51] Int. Cl.³ .................... A01N 37/40; C07C 79/46
[52] U.S. Cl. ..................................... 71/108; 71/105;
             71/111; 560/21; 560/65; 260/465 D
[58] Field of Search .............. 560/21, 65; 260/465 D;
                                           71/108, 105, 111

[56] References Cited

U.S. PATENT DOCUMENTS

| | | | |
|---|---|---|---|
| 2,818,424 | 12/1957 | Zeile et al. | 71/108 |
| 3,784,635 | 1/1974 | Theissen | 260/471 |
| 3,798,276 | 3/1974 | Bayer et al. | 260/612 |
| 4,093,446 | 6/1978 | Bayer et al. | 560/21 |
| 4,134,753 | 1/1979 | Hörlein et al. | 560/21 |
| 4,209,318 | 6/1980 | Johnson | 560/21 |

*Primary Examiner*—G. T. Breitenstein
*Attorney, Agent, or Firm*—Edward J. Whitfield

[57] ABSTRACT

This invention concerns certain substituted diphenyl ethers having herbicidal activity, their preparation, and the control of weeds therewith.

8 Claims, No Drawings

SUBSTITUTED DIPHENYL ETHERS HAVING HERBICIDAL ACTIVITY

FIELD OF THE INVENTION

This invention concerns certain substituted diphenyl ethers having herbicidal activity, their preparation, and the control of weeds therewith.

DESCRIPTION OF THE INVENTION

This invention concerns substituted diphenyl ethers which, in one embodiment, are represented by the formula:

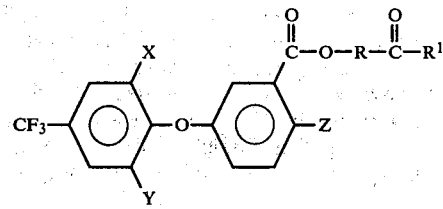

wherein:
X is hydrogen or halogen;
Y is hydrogen, halogen, cyano, trifluoromethyl, or alkyl containing 1 to 4 carbon atoms;
Z is nitro;
R is alkylidene or monosubstituted alkylidene containing 1 to 3 carbon atoms wherein the substituent is alkyl containing 1 to 4 carbon atoms; and
$R^1$ is hydrogen or alkyl containing 1 to 10 carbon atoms.

This invention also concerns substituted diphenyl ethers which, in another embodiment, are represented by the above formula, wherein X, Y, R, and $R^1$ are as above defined, but wherein Z is halogen or cyano.

Exemplary of halogens represented by the various substituents in the above formula are bromine, chlorine, iodine, or fluorine, preferably bromine or chlorine. Some alkyl groups suitable as substituents in the above formula are, for example, methyl, ethyl, n-propyl, isopropyl, n-butyl, isobutyl, t-butyl, n-amyl, heptyl, octyl, isooctyl, nonyl, decyl, and the like. As alkylidene radicals there may be mentioned methylidene, ethylidene, and propylidene. Preferred compounds in accordance with this invention are those wherein X is hydrogen; Y is halogen, e.g. chlorine; Z is nitro; and $R^1$ is alkyl of 1 to 4 carbon atoms. 2'-Oxopropyl 5-(2-chloro-4-trifluoromethylphenoxy)-2-nitrobenzoate is exemplary of a preferred compound of this invention.

Compounds of the above formula are believed to have herbicidal activity in accordance with this invention. Those compounds wherein the 'Z' substituent is other than nitro, e.g. halogen, are belived to be somewhat more herbicidally active when applied postemergent rather than preemergent. Those compounds wherein the 'Z' substituent is nitro have been generally found effective when applied either pre- or postemergent; however, at lower levels of application, i.e. 2 pounds per acre or less, somewhat better postemergent activity appears to be exhibited.

It is of course to be understood that the stereo and optical isomers of compounds represented by the above formula are within the scope of this invention.

The compounds of this invention are typically synthesized by reacting an appropriately substituted benzoyl halide of the formula:

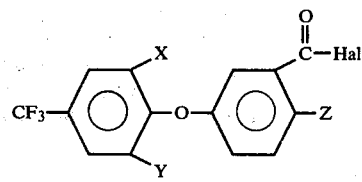

wherein X, Y, and Z are as previously defined and Hal is halogen, preferably chlorine or bromine, with an at least stoichiometric amount of an appropriately hydroxy substituted ketone or aldehyde of the formula:

wherein R and $R^1$ are as previously defined, using techniques known to the art. The substituted benzoyl halides and ketone or aldehyde may be obtained from commercial sources or prepared by known techniques.

More particularly, an at least stoichiometric amount of substituted benzoyl halide is added, with stirring, to the ketone or aldehyde, preferably in the presence of an acid acceptor, such as, for example, triethylamine, pyridine, N,N-dimethylaniline or the like. Since the reaction is exothermic, the substituted benzoyl halide is added incrementally so that the temperature of the reaction mixture does not appreciably exceed about 35° C. If desired, either or both the substituted benzoyl halide and the ketone or aldehyde may be dissolved in an inert solvent, such as, for example, benzene, methylene chloride, chloroform, ethyl acetate, tetrahydrofuran, or the like. At the completion of addition of the substituted benzoyl halide, the reaction mixture is heated to reflux and maintained at reflux until the reaction reaches the desired degree of completion. The reaction mixture is then cooled to ambient temperature and washed typically consecutively with dilute mineral acid, dilute caustic and water, and allowed to phase separate. Substituted diphenyl ether is recovered from the organic phase by any known technique, such as, for example, evaporation, crystallization, vacuum drying or the like. If desired, the product, substituted diphenyl ether, may be further purified by, for example, recrystallization.

The following Example is illustrative of the synthesis of a specific substituted diphenyl ether compound of this invention.

EXAMPLE

2'-Oxopropyl 5-(2-chloro-4-trifluoromethylphenoxy)-2-nitrobenzoate

A three-necked 100 milliliter flask equipped with an addition funnel, a reflux condenser, and a magnetic stirring bar was charged with a solution of 0.74 gram (0.01 mole) of hydroxy acetone and 1.1 grams (0.01 mole) of triethylamine in 30 milliliters of benzene. To this stirred solution at ambient temperature, a solution of 3.79 grams (0.01 mole) of 5-(2-chloro-4-trifluoromethylphenoxy)-2-nitrobenzoyl chloride in 20 milliliters of benzene was added dropwise. Exothermic heating was observed. Upon completion of the addition, the reaction mixture was refluxed overnight (about 20 hours), cooled and then transferred to a separatory funnel. The reaction mixture was then washed with 30 milliliters each of 1 Normal hydrochloric acid, water, 1 Normal sodium hydroxide solution and water, respectively. The organic phase was removed, dried over anhydrous magnesium sulfate and concentrated on a rotary evaporator at 55° C., yielding 3.1 grams of a light brown syrupy liquid which was identified as 2'-oxopropyl 5-(2-chloro-4-trifluoromethylphenoxy)-2-nitrobenzoate having:

NMR (d$_6$): 7.18–8.2δ (multiplet, 6H); 4.95δ (singlet, 2H); 2.15δ (singlet, 3H).

The mode of synthesis of a specific compound of this invention has been illustrated by the foregoing Example, but it is to be understood that any compound contemplated to be within the scope of this invention may be prepared by those skilled in the art simply by varying the choice of starting materials and using the illustrated technique or other suitable techniques.

The compounds of this invention are believed effective in regulating the growth of a variety of undesirable plants, i.e. weeds, when applied, in an herbicidally effective amount, to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, method of application, and the like. Typically, as little as 0.2 or less pound per acre to 10 or more pounds per acre of compound or mixtures of compounds may be required. Of course, the efficacy of a particular compound against a particular weed species may readily be determined by relatively straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, stabilizers, safeners, fertilizers, and the like. The compounds of this invention, whether or not in formulation with other agronomically acceptable materials, are typically applied in the form of dusts, granules, wettable powders, solutions, suspension, aerosols, emulsions, dispersions or the like in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically such formulations will contain from about 5 to about 75 percent by weight of compound or compounds of this invention.

Certain of the compounds of this invention have been found effective in controlling a variety of broadleaf and grassy weeds at application rates of two pounds per acre or less pre- or postemergence while not significantly damaging desirable crops such as, for example, corn, cotton, and soybeans. Exemplary of weeds that may be effectively controlled by the application of compounds of this invention are wild mustard (Brassica kaber); yellow foxtail (Setaria glauca); crabgrass (Digitaria sanguinalis); coffeeweed (Sesbania spp.); velvetleaf (Abutilon theophrasti); johnsongrass (Sorghum halepense); barnyardgrass (Echinochloa crusgalli); jimsonweed (Datura stramonium); teaweed (Sida spinosa); tall morningglory (Roth); and the like.

The compound prepared according to the Example was tested for herbicidal activity against certain weed species under controlled laboratory conditions of light, temperature, and humidity. Seeds of selected weeds were planted in flats. For preemergence tests, the flats were treated with the selected compound immediately after planting. For postemergence tests, the flats were treated with the selected compound after a two-week germination period. The compound was applied to the flats at a rate of 2 pounds per acre by spraying a solvent solution of the compound. The state of growth of the weeds was observed, and the toxic effect of the compound was evaluated periodically after application. The following shows in tabular form the weed species (identified by common name), to which weed species the compound was applied (indicated by an "X"), and whether the application was pre- or postemergent.

| Weed | Application of Example Compound | |
|---|---|---|
| | Preemergent | Postemergent |
| Jimsonweed | X | X |
| Wild mustard | X | X |
| Yellow foxtail | X | |
| Crabgrass | X | |
| Johnsongrass | X | X |
| Coffeeweed | | X |
| Velvetleaf | | X |
| Tall morningglory | | X |
| Barnyardgrass | X | |

In each of the foregoing tests, it was observed that all of the various weeds were either killed or injured beyond recovery within 22 days after application of the compound. Although the invention has been described in considerable detail with reference to illustrative embodiments thereof, it is to be understood that it is not intended to be so limited since many variations may be made therein by those skilled in the art without departing from the spirit and scope thereof as defined in the appended claims.

I claim:

1. A compound represented by the formula:

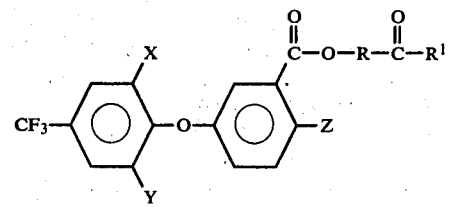

wherein:
X is hydrogen or halogen;
Y is hydrogen, halogen, cyano, trifluoromethyl, or alkyl containing up to 4 carbon atoms;
Z is nitro, halogen, or cyano;
R is alkylidene or monosubstituted alkylidene containing 1 to 3 carbon atoms wherein the substituent is alkyl containing 1 to 4 carbon atoms; and
R$^1$ is hydrogen or alkyl containing 1 to 10 carbon atoms.

2. The compound of claim 1 wherein Z is nitro.

3. The compound of claim 1 wherein Z is halogen or cyano.

4. The compound of claim 1 wherein X is hydrogen, Y is halogen, and Z is nitro.

5. The compound of claim 1 wherein $R^1$ is alkyl containing 1 to 4 carbon atoms.

6. The compound of claim 1 wherein X is hydrogen, Y is chlorine, Z is nitro, R is methylidene, and $R^1$ is methyl.

7. A herbicidal formulation containing an inert carrier and a herbicidally effective amount of a compound or mixture of compounds defined in claim 1.

8. In a method of controlling weed growth wherein a herbicidally effective amount of herbicide is either applied to the growth medium prior to emergence of the weeds or applied to the weeds subsequent to emergence from the growth medium, wherein the improvement resides in using as the herbicide a herbicidally effective amount of a compound or mixture of compounds defined in claim 1.

* * * * *

REEXAMINATION CERTIFICATE (1070th)

United States Patent [19]

Grove

[11] B1 4,311,515

[45] Certificate Issued    Jun. 6, 1989

[54] SUBSTITUTED DIPHENYL ETHERS HAVING HERBICIDAL ACTIVITY

[75] Inventor: William S. Grove, Doylestown, Ohio

[73] Assignee: PPG Industries, Inc., Pittsburgh, Pa.

Reexamination Request:
No. 90/000,586, Jul. 9, 1984

Reexamination Certificate for:
Patent No.: 4,311,515
Issued: Jan. 19, 1982
Appl. No.: 172,319
Filed: Jul. 25, 1980

[51] Int. Cl.$^4$ .................. A01N 37/40; C07C 79/46

[52] U.S. Cl. ........................... 71/108; 71/105; 71/111; 560/21; 560/65; 260/465 D

[58] Field of Search ............... 560/21, 65; 260/465 D; 71/108, 105, 111

[56] References Cited

U.S. PATENT DOCUMENTS

| | | | |
|---|---|---|---|
| 3,137,563 | 6/1964 | Newcomer | 71/2.6 |
| 3,282,991 | 11/1966 | Klein et al. | 71/107 |
| 3,325,274 | 6/1967 | Anderson | 71/2.6 |
| 4,063,929 | 12/1977 | Bayer et al. | 71/115 |

*Primary Examiner*—Paul J. Killos

[57] ABSTRACT

This invention concerns certain substituted diphenyl ethers having herbicidal activity, their preparation, and the control of weeds therewith.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *